(12) United States Patent
Caruth

(10) Patent No.: US 9,284,095 B2
(45) Date of Patent: Mar. 15, 2016

(54) OPHTHALMIC MEDICATION AND TREATMENT CASE

(71) Applicant: Debbie Joanne Caruth, Elmont, NY (US)

(72) Inventor: Debbie Joanne Caruth, Elmont, NY (US)

( * ) Notice: Subject to any disclaimer, the term of this patent is extended or adjusted under 35 U.S.C. 154(b) by 172 days.

(21) Appl. No.: 13/741,521

(22) Filed: Jan. 15, 2013

(65) Prior Publication Data
US 2013/0277247 A1 Oct. 24, 2013

Related U.S. Application Data

(60) Provisional application No. 61/637,591, filed on Apr. 24, 2012.

(51) Int. Cl.
| | |
|---|---|
| *B65D 69/00* | (2006.01) |
| *B65D 33/00* | (2006.01) |
| *A45C 3/02* | (2006.01) |
| *A61B 19/02* | (2006.01) |
| *A45C 7/00* | (2006.01) |
| *A61J 1/16* | (2006.01) |
| *A45C 11/00* | (2006.01) |

(52) U.S. Cl.
CPC . *B65D 33/00* (2013.01); *A45C 3/02* (2013.01); *A61B 19/0264* (2013.01); *A45C 7/0095* (2013.01); *A45C 2011/007* (2013.01); *A61B 2019/0278* (2013.01); *A61B 2019/0286* (2013.01); *A61J 1/16* (2013.01)

(58) Field of Classification Search
CPC ...... B65D 33/00; A45C 3/02; A61B 19/0264; A61B 2019/0286; A61B 2019/0278
USPC .......... 206/38, 232, 472–475, 425, 528, 538, 206/540, 570; 62/371, 457.1, 457.2; 229/67.1, 67.3, 67.4; 383/38–40
See application file for complete search history.

(56) References Cited

U.S. PATENT DOCUMENTS

| | | | |
|---|---|---|---|
| 2,807,265 A | 9/1957 | Oliva et al. | |
| 4,343,158 A | 8/1982 | Campbell | |
| 4,429,793 A | 2/1984 | Ehmann | |
| 5,012,931 A | 5/1991 | Ferrera | |
| 5,114,259 A | 5/1992 | Meservy et al. | |
| 5,118,213 A | 6/1992 | Meservy et al. | |

(Continued)

OTHER PUBLICATIONS

Feb. 3, 2014 Non-Final Office Action for U.S. Appl. No. 13/741,514.
(Continued)

*Primary Examiner* — Luan K Bui
(74) *Attorney, Agent, or Firm* — Daniel Boudwin; Global Intellectual Property Agency, LLC.

(57) ABSTRACT

Disclosed is a medication carrying case having a modular interior and a deployable tray work surface specifically designed for those having ophthalmic conditions or recovering from procedures related to the eyes. The case structure is provided in several different sizes and designs, whereby eye medication and treatment articles are supported by removably attached organizational leaflets attached along the interior surfaces of the case flaps. Each leaflet comprises a number of different transparent and optically magnified pouches for supporting articles therein, whereby a user with diminished vision can readily locate an article without interrogating each pouch individually. A deployable tray attaches along the exterior of the case and provides a clean work surface for organizing and preparing medication prior to use.

7 Claims, 4 Drawing Sheets

(56) References Cited

U.S. PATENT DOCUMENTS

| | | | |
|---|---|---|---|
| 5,226,532 A * | 7/1993 | Davidson et al. | 206/232 |
| D338,781 S | 8/1993 | Eitel | |
| 5,232,301 A * | 8/1993 | Bianco | 402/73 |
| 5,598,923 A * | 2/1997 | Owens | 206/370 |
| 5,610,770 A * | 3/1997 | Galiani | 206/37 |
| D383,306 S | 9/1997 | Pennoyer | |
| 5,865,314 A | 2/1999 | Jacober | |
| 5,911,441 A * | 6/1999 | Yamamoto et al. | 281/15.1 |
| 5,931,303 A * | 8/1999 | Salvadori | 206/570 |
| 6,095,564 A * | 8/2000 | Wien | 281/15.1 |
| 6,109,442 A * | 8/2000 | Roegner | 206/581 |
| 6,249,390 B1 | 6/2001 | Thibodeaux, Jr. | |
| 6,253,570 B1 | 7/2001 | Lustig | |
| 6,454,097 B1 | 9/2002 | Blanco | |
| 6,491,074 B1 | 12/2002 | Roegner | |
| D505,543 S | 5/2005 | Miller | |
| 6,935,133 B2 | 8/2005 | Keeter et al. | |
| 6,959,814 B1 | 11/2005 | Hyman | |
| D562,547 S | 2/2008 | Mesalic et al. | |
| 7,565,979 B1 | 7/2009 | Gibson | |
| D619,801 S | 7/2010 | Ma et al. | |
| 8,006,846 B2 | 8/2011 | Robertson | |
| 2003/0211617 A1 | 11/2003 | Jones | |
| 2006/0006097 A1 | 1/2006 | Peacock | |
| 2008/0141700 A1 * | 6/2008 | Fuchs | 62/371 |
| 2009/0107876 A1 | 4/2009 | Bengtson | |
| 2010/0133139 A1 * | 6/2010 | Lowe | 206/534 |
| 2011/0097017 A1 * | 4/2011 | Abrams | 383/40 |

OTHER PUBLICATIONS

Oct. 15, 2014 Non-Final Office Action for U.S. Appl. No. 13/741,514.

Jun. 18, 2015 Final Office Action for U.S. Appl. No. 13/741,514.

Jan. 12, 2016 Non-Final Office Action for U.S. Appl. No. 13/741,514.

\* cited by examiner

OPHTHALMIC MEDICATION AND TREATMENT CASE

CROSS REFERENCE TO RELATED APPLICATION

This application claims the benefit of U.S. Provisional Application No. 61/637,591 filed on Apr. 4, 2012, entitled "Ophthalmic-Kit." The above identified patent application is herein incorporated by reference in its entirety to provide continuity of disclosure.

BACKGROUND OF THE INVENTION

1. Field of the Invention

The present invention relates to a medical carrying case for the visually impaired, including those with eye injuries, those recovering from eye surgery, and those with general visual impairment or ophthalmic conditions. More specifically, the present invention pertains to a carry case or binder having a modular interior to support articles within transparent and optically magnified pouches for increased clarity.

For those with visual impairments, locating and carrying medical treatment articles can be difficult. Reduced vision makes it more difficult to track each treatment item, organize the items, and prevent items from being mixed prior to administration. These individuals include those with general visual impairment taking medication, those patients recovering from eye surgery procedures, and those with ophthalmic conditions that limit their vision. The ability to effectively administer medication and treatment regimes can be hindered if one cannot correct visualize or locate the items.

For those individuals requiring regular doses of medication to maintain their health, visual impairment can reduce compliance with administration of the medication if it is not efficiently organized and readily available. Specific dosages of certain medication may be required throughout the day, either because of a precipitating event or based on a prescribed interval. Organizing, storing and efficiently carrying medication while also providing increased clarity of each item greatly increases compliance and one's ability to choose appropriate medication. Self-administered medication requires a careful eye for correct dosages, requires taking proper measures to adequately store the medication, and further requires the user to take the medication on the correct schedule and thus have it handy on the go if necessary. If patients are unable to take their required medication on a regular schedule or during an emergency event, the patient may be opening themselves up to greater health risks and even life threatening conditions. Further still, those patients that are not consistent with their medication can cause problems for healthcare providers when assessing the patient's proper needs and progress with a given medication type.

The primary issues are transporting medication and treatment articles and efficiently organizing each article in a manner that allows a user to readily recognize and distinguish each article. For those patients requiring administration of medication throughout the day, a means of storing, organizing and efficiently traveling with the required medication is critical to ensure the medication is available when necessary and taken on schedule. The medication should be stored in recognizable containers and separated from one another, particularly if more than one type is necessary for the user. While traveling, the articles should be readily visible to the user, particularly for those with visual impairments. Transparent and optically enhancing containers provide a means to improve recognition of each article and reduce dosage mistakes or swapped medications.

The present invention comprises a medical treatment carrying case that provides adequate and efficient storage for its medical contents for the visually impaired. The device comprises several embodiments for its design; however the case utility involves internal organizational leaflets having translucent and optically enhances pouches for supporting articles therein. Those with visual impairments, those recovering from an eye injury or procedure, or those with general eye conditions requiring treatment would be benefited, whereby each pouch separates a type of medication or article, while the user can readily identify and locate each article without closely inspecting each pouch. The case is provided in different sizes and case configurations for the user to easily carry all necessary medication while on the go and deploy the medication when necessary in a given environment or over the course of a day.

2. Description of the Prior Art

Devices have been disclosed in the prior art that relate to medication cases and storage means. These include devices that have been patented and published in patent application publications, and generally relate to medicine container carrying cases and insulin carrying cases. While many cases are known in the art for carrying items, and in particular medication items, the present invention provides several key improvements that sufficient distinguish the present invention from those items in the prior art, while fulfilling a need for an efficient and useful medication carrying case device for users. The following is a list of devices deemed most relevant to the present disclosure, which are herein described for the purposes of highlighting and differentiating the unique aspects of the present invention, and further highlighting the drawbacks existing in the prior art.

U.S. Pat. No. 5,610,770 to Galiani discloses a lens magnification system provided for optically enhancing flat articles, whereby the device comprises a flat sheet type lens supported within a booklet support. The lens is supported by a pivoting frame that connects to the booklet and allows the frame to be moved relative to the planar object being magnified, such as a menu or article of paper. The system provides a visually impaired individual to more easily view and read an article without requiring eyeglasses. While novel and unique, the Galiani device fails to disclose a carrying case having a plurality of transparent and optically enhanced pouches that allow for efficient storage and location of medical items.

U.S. Pat. No. 6,095,564 to Wien discloses a partitioned binder assembly having a spine, covers, an intermediate cover, a ring binder and a plurality of separate storage arrangements. The storage arrangements comprise several different storage options for the user, including a file folder, a calculator storage arrangement, a loop for holding writing utensils and other arraignments adapted to provide the user with storage for productivity tools and school supplies. The Wien device, while disclosing a binder having a folded construction and interior storage for articles, fails to disclose a working embodiment that is adapted to secure medication and treatment articles in a clear and optically enhanced manner for those with visual impairments or injuries.

U.S. Pat. No. 6,249,390 to Thibodeaux, Jr. discloses a binder insert having magnifying properties. The binder insert is a planar sheet having apertures for securing to a binder, while the body of the insert includes a Fresnel lens for magnifying small or unreadable indicia on pages thereunder. Along one edge of the insert may further be positioned measurement indicia so the device may be overlaid over another sheet for use as a measuring tool. This insert, while providing improved clarity of objects thereunder, fails to disclose a binder having pouches made from optically enhanced material to magnify objects within the pouch.

Finally, U.S. Patent Application Publication No. 2009/0107876 to Bengston discloses a post-surgical accessory kit to serve a patient's post-operative needs. The kit comprises a carrier or pouch adapted to be worn around a patient's waist. The pouch includes a plurality of pockets and a length of tubing adapted to couple with a reservoir for collecting draining fluid from the wound or drainage site on the patient. Similar to the aforementioned devices, the Bengston device fails to provide a carrier means that is adapted for post-surgical procedures or ailments related to vision.

The present invention provides a medication carrying case and binder that provides increased clarity of the items being supported. The device comprises a binder or carrying case having internal leaflets for supporting articles of medication and medical equipment. Each pouch comprises a transparent, optically enhanced outer layer that magnifies the contents therein. The goal is to provide those with visual impairments and those recovering from eye surgeries to readily recognize required medication in a convenience and modular carrying case. The design of the present invention is disclosed having several embodiments, allowing for a compact case with efficient carrying of medical supplies, as well as larger, more accommodating carrying cases for greater amounts of needed medical supplies while traveling. It is submitted that the present invention is substantially diverges in design elements from the prior art, and consequently it is clear that there is a need in the art for an improvement to existing medical carrying case devices. In this regard the instant invention substantially fulfills these needs.

SUMMARY OF THE INVENTION

In view of the foregoing disadvantages inherent in the known types of medical carrying cases now present in the prior art, the present invention provides a new and improved carrying case having magnification means therein such that the case can be utilized for providing convenience for a user with impaired vision.

It is therefore an object of the present invention to provide a new and improved medical carrying case device that has all of the advantages of the prior art and none of the disadvantages.

It is another object of the present invention to provide a medical carrying case device that comprises a number of different sizes and designs for the purposes of providing efficient storage of medicine and medical supplies while traveling.

Another object of the present invention is to provide a medical carrying case device having a plurality of interior leaflets adapted to support medication and medical treatment articles in an efficient, organized and modular arrangement.

Yet another object of the present invention is to provide a medical carrying case device that employs internal medication support leaflets having transparent and magnifying pouches, whereby the contents of each pouch is optically enhanced for those with visual impairments to more easily see each article therein.

Still yet another object of the present invention is to provide a medical carrying case device that includes a deployable tray that allows a user to deploy, sort and visualize medication on a clean support surface prior to administration of the medication.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
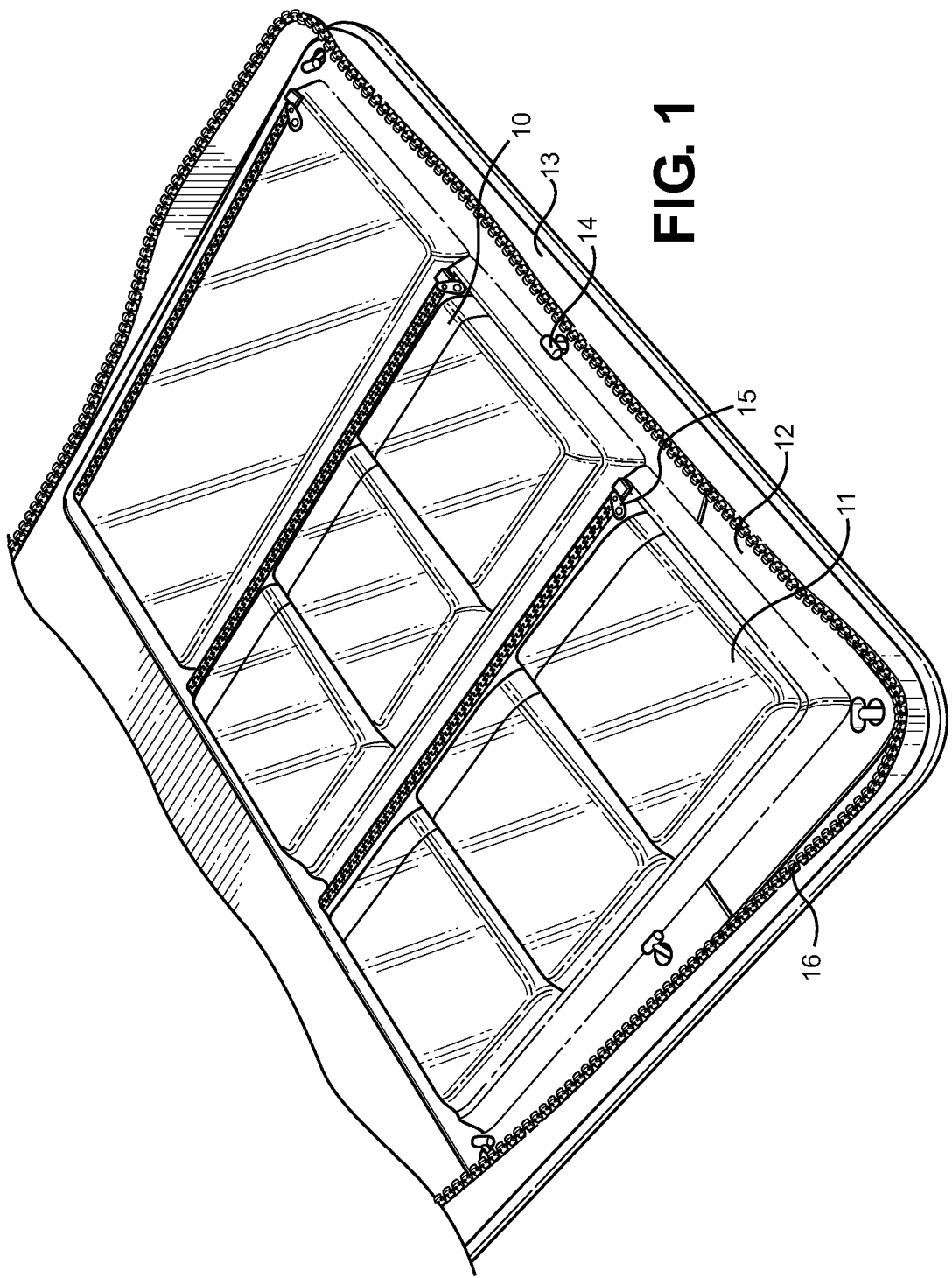
FIG. 1 shows a perspective view of the present invention in an open configuration, showing the transparent pouches of the internal leaflets.

Reference is made herein to the attached drawings. Like reference numerals are used throughout the drawings to depict like or similar elements of the medical carrying case. For the purposes of presenting a brief and clear description of the present invention, the preferred embodiment will be discussed as used for carrying insulin and medication while traveling. The figures are intended for representative purposes only and should not be considered to be limiting in any respect.

Referring now to FIG. 1, there is shown a perspective view of the internal organizational elements of the present invention, where the carrying case is in an open state for viewing its contents. The carrying case comprises an article of luggage, where its design ranges from a handheld binder having a first and second joined flap, to larger embodiments having several collapsing flaps. FIG. 1 shoes the interior of a carrying case flap 13, where the flap comprises an exterior surface, an interior surface, a boundary securement means 16, and an internal edge forming the binding of the case or connection with an adjacent case flap. The boundary securement means 16 forms a line of connection around the perimeter edge of the flap, which is preferably a zip fastener closure structure to secure the flap closed against and adjacent flap.

Along the interior surface of each case flap is at least one organizational leaflet 12 secured thereto using an appropriate connector element 14 along its perimeter. The leaflet 12 is a planar surface having a plurality of medication and equipment pouches 11 secured thereto and facing inward from the case flap 13. Each of the pouches 11 comprises a transparent outer layer that is adapted to provide a user with visual access into the pouch interior, such that the articles can be seen without interrogating then individually. The transparent outer layer further provides increased optical clarity and magnification of its interior. To further aid those patients with visual impairments or those recovering from eye surgery, the structure of the pouches incorporates a magnification means, such as a Fresnel lens or other suitable lens structure that increases the optical clarity and magnifies the interior space to an outside observer. This magnification allows one with reduced visual acuity to locate medication without accessing each pouch interior and individually inspecting the articles by hand.

Figure 4:
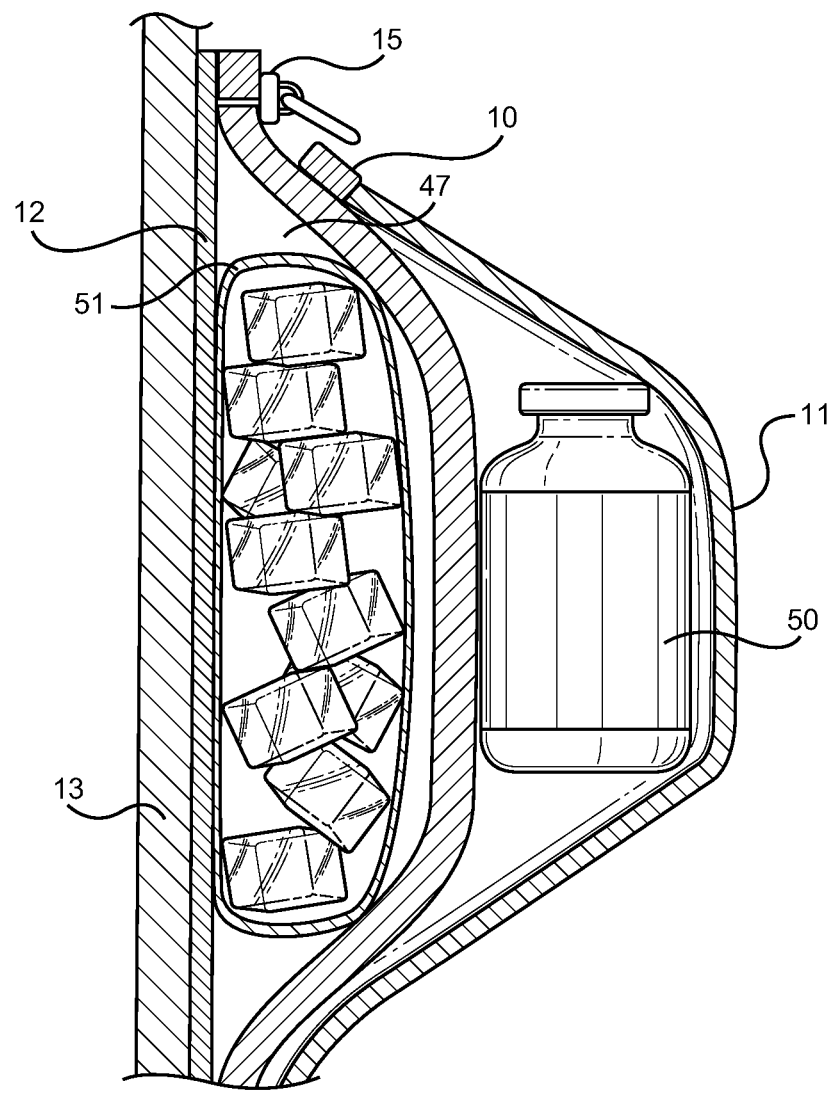
FIG. 4 shows a cross section view of an alternative embodiment of the present invention, whereby a rear cavity within the leaflets provides storage for a cooling means.

The pouches 11 include an open upper 10 having an elastic structure or securement means to prevent the opening from spilling the pouch contents while traveling. The elastic structure biases the pouch opening 10 against the leaflet, while the alternative securement means secures the opening in a closed position. Just below the opening 10 may be provided an insert for placing a label therein, whereby the label is visible the user while the article is readily visible through the outer layer of the pouch. In a further alternative, and as shown in FIGS. 1 and 4, a secondary cavity 47 behind the pouches 11 is secured closed by a zip fastener securement means 15. This alternative structure provides a cavity 47 for placement of cooling means 51, such as ice packs, for storing temperature sensitive items within the pouches 11. Medication such as insulin 50 can therefore be stored within the pouches 11 and cooled by the cooling means 51 within the cavity 47 between the pouch and the leaflet surface 12. The cavity 47 is separated from the flap interior 13 and the interior of the case, whereby condensation and moisture does not contact any of the carrying case interior contents or structure, and is retained within the rear cavity 47.

Figure 2:
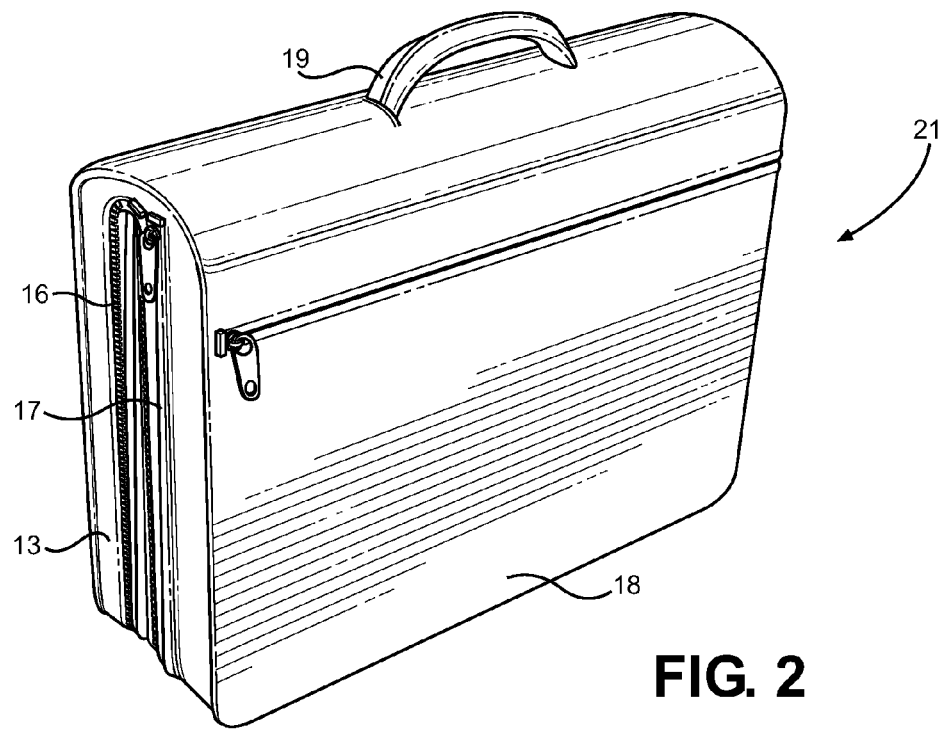
FIG. 2 shows the binder embodiment of the present carrying case.

Referring now to FIG. 2, there is shown an external view of the preferred design of the present carrying case 21. In this embodiment, the case comprises a first 13 and second 18 case flap that are joined together along a common binding to form a folding binder structure. The flaps 13, 18 are secured along three of their perimeter edges via a zip fastener line of connection 16, while a handle 19 and optional shoulder strap is positioned along the binding. To allow for increased carrying capacity, an expansion zipper 17 is positioned adjacent to the flap zipper 16, whereby unzipping this zipper 17 allows the structure to expand as is well understood in the art of suitcases and luggage articles. The edges of the zipper 17 separate and are held together only by an internal section of material, which allows the interior of the case 21 to expand for increased storage of articles therein.

Figure 3:
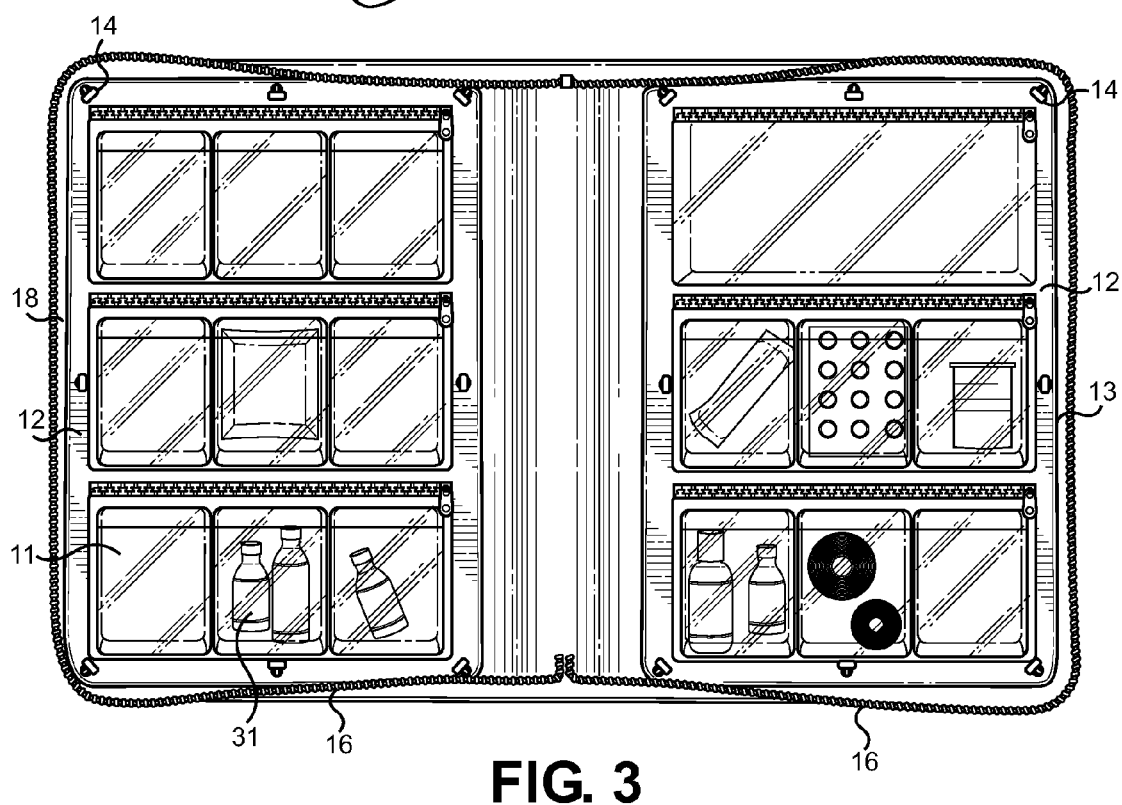
FIG. 3 is a front view of the binder embodiment in an open configuration.

Referring now to FIG. 3, there is shown a view of the present carrying case in an open position, displaying its internal organizational leaflets and their transparent and magnified structure. The transparency of the pouches 11 allows for items 31 to be readily viewed when opening the case, while the magnification improves the clarity and the apparent size of the interior contents for those with visual impairments. In this embodiment, the carrying case comprises a dual flap 13, 18 structure having a single line of connection 16 for form a binder structure. Along the interior surfaces of each flap is a first and second removable leaflet 12 that is secured with peripheral snaps, hooks or similarly appropriate connector elements. The leaflets 12 are removable from the interior of the case and interchangeable with alternate leaflets. This offers different pouch layouts for the user, whereby the user can swap out existing leaflets for others to meet the needs of the particular user and the particular treatment type.

Figure 5:
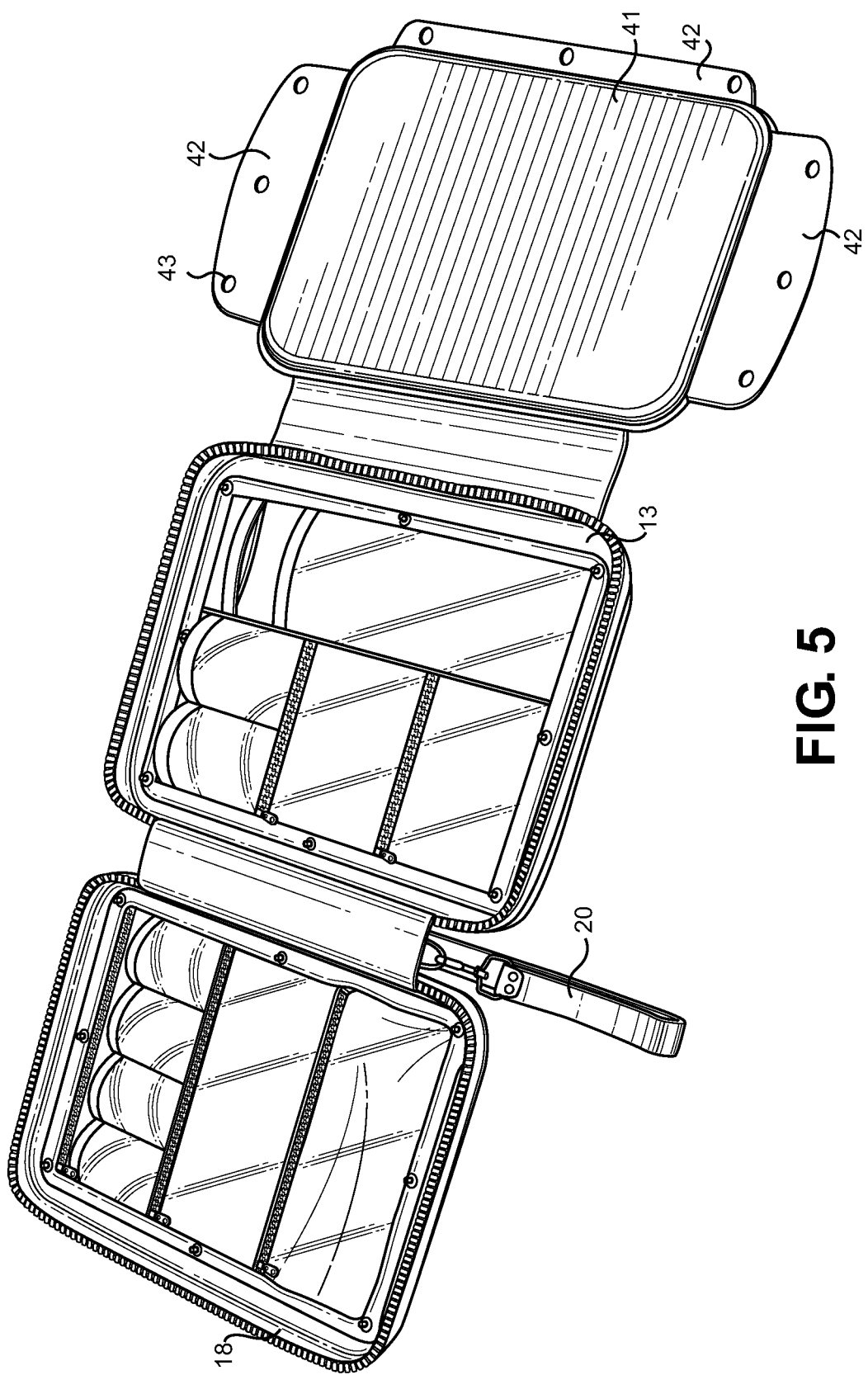
FIG. 5 shows the binder embodiment in an open configuration and the deployable tray in a working position.

Referring now to FIG. 5, there is shown an alternate design of the present invention, along with a deployable tray surface 41 that secures about the exterior of one of the case flaps. The tray 41 is deployable from the outer surface of one of the case flaps 13, whereby the case opens towards the inner surface of the tray 41 for withdrawing medication and supplies directly thereonto. When stowed, the tray 41 is placed against the exterior of the case and secured thereto using a plurality of securement members 42. The securement members 42 include snaps 43 or similar connection means thereon, where corresponding connectors 43 are positioned along the exterior of the case to retain the tray 41 in a stowed condition against the case exterior. The tray securement members are elastic members that extend outward from the perimeter of the tray 41 along at least one side. Corresponding securement snaps 43 positioned about the case exterior to prevent the tray from inadvertently deploying when the user is transporting the case. The tray 41 therefore remains attached to the case along its lower edge when deployed, or alternatively the tray 41 may be completely removed therefrom to provide an independent medication tray for the user. This lower edge connection may also comprise snap securement elements in the same fashion as the other tray flap connectors 43.

Each embodiment of the case includes modular leaflets along the interior surface of each case flap, while the overall style and size of the case may vary between designs. Larger embodiments of the case comprise several flaps the form compartments connected to one another, establishing a single fold, two fold or multiple-fold structure having aligned and accessible compartments. Each compartment includes a pair of opposed interior surfaces supporting the leaflets, whereby the compartments are individually accessed via a zipper closure along a line of connection between flaps. The design of the interior leaflets may also be a design consideration, where the arrangement of pockets and each pocket may include unique qualities for securing items within the case. The exterior of the case can be designed to be rugged, fashionable, or utilitarian, as desired by the end user. Similarly, an external handle and carrying strap 20 may be provided to transport the device with supported articles therein.

Overall, the present invention provides a new and novel carrying case that efficiently organizes medication and medical supplies for individuals traveling outside of the home. The case simplifies a user's process of organizing and dispensing medication throughout the day, while also providing a means of improving clarity of each supported item within magnified pouches. The structure of the case is at least two opposing case flaps that form the case structure, wherein organizational leaflets are provided along the interior surface of each leaflet and a deployable tray offers a work space for the user. The size of the case and its design elements may be tailored to a specific user's needs for different carrying capacities and styles of case. The primary purpose of the case, however, is to efficiently transport medication, improved optical clarity of supported items, and quick access to the medication while traveling.

It is submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A medication carrying case, comprising:

at least two opposing case flaps forming a structure having an interior volume wherein said opposing case flaps are joined by a zippered line of connection;

said opposing case flaps each having an interior surface and an exterior surface;

an organizational leaflet having at least one pouch thereon that is removably attached to the interior surface of one of said opposing case flaps;

wherein said at least one pouch comprises an outer flap layer forming an interior volume between the outer flap layer and the organization leaflet, said outer flap layer being transparent and comprising a magnification lens such that articles within said at least one pouch are optically magnified to an outside observer;

each pouch having a backside cavity adapted for supporting a cooling element therein;

said backside cavity comprising a moisture sealed cavity disposed between the organizational leaflet and each pouch.

2. The medication carrying case of claim 1, wherein magnification lens of the outer flap layer comprises a Fresnel lens.

3. The medication carrying case of claim 1, further comprising:

a deployable tray coextensive with at least one case flap exterior surface being pivotable therefrom, said tray having an exterior surface and an interior surface, said interior surface forming a work surface when deployed.

4. The medication carrying case of claim 1, wherein said organizational leaflet comprises a substantially planar structure, wherein said at least one pouch comprises an elastic and open upper to removably support articles therein.

5. The medication carrying case of claim 1, wherein:

said organizational leaflet comprises a substantially planar structure; and wherein said backside cavity is coextensive with said at least one pouch.

6. The medication carrying case of claim 1, further comprising an expansion zipper along one of said opposing case flaps for expanding said interior volume.

7. The medication carrying case of claim 1, wherein each backside cavity further comprises an opening with a zip fastener securement.

* * * * *